(12) United States Patent
Petersen et al.

(10) Patent No.: US 9,913,766 B2
(45) Date of Patent: Mar. 13, 2018

(54) SANITARY PRODUCT SYSTEM

(75) Inventors: Johann F. Petersen, Grevenbroich (DE); Volker Hauschildt, Hilden (DE); Peter Kitzer, Echt (DE); Thomas Hertlein, Korschenbroich (DE)

(73) Assignee: 3M Innovative Properties Company, St. Paul, MN (US)

( * ) Notice: Subject to any disclaimer, the term of this patent is extended or adjusted under 35 U.S.C. 154(b) by 644 days.

(21) Appl. No.: 14/232,387

(22) PCT Filed: Jul. 12, 2012

(86) PCT No.: PCT/US2012/046424
§ 371 (c)(1),
(2), (4) Date: Mar. 17, 2014

(87) PCT Pub. No.: WO2013/009964
PCT Pub. Date: Jan. 17, 2013

(65) Prior Publication Data
US 2014/0213996 A1   Jul. 31, 2014

(30) Foreign Application Priority Data

Jul. 13, 2011 (EP) ..................... 11173789

(51) Int. Cl.
*A61F 13/15* (2006.01)
*A61F 13/58* (2006.01)
(Continued)

(52) U.S. Cl.
CPC ........ *A61F 13/581* (2013.01); *A61F 13/5605* (2013.01); *A61F 13/60* (2013.01);
(Continued)

(58) Field of Classification Search
CPC ............ A61F 13/505; A61F 2013/5055; A61F 13/581; A61F 13/5605; A61F 13/60; A61F 13/622; A61F 13/665
(Continued)

(56) References Cited

U.S. PATENT DOCUMENTS

| | | |
|---|---|---|
| 3,192,589 A | 7/1965 | Pearson |
| 3,408,705 A | 11/1968 | Kayser et al. |

(Continued)

FOREIGN PATENT DOCUMENTS

| | | |
|---|---|---|
| EP | 0 341 993 A1 | 5/1989 |
| EP | 0 549 705 B1 | 8/1991 |

(Continued)

OTHER PUBLICATIONS

US 5,389,416, 02/1995, Mody et al. (withdrawn)

*Primary Examiner* — Jacqueline Stephens
(74) *Attorney, Agent, or Firm* — Steven A. Bern; Lynn R. Hunsberger

(57) ABSTRACT

This invention is directed to a sanitary product attachment means comprising a connection member (3) having a flexible base carrier (4), whereas on one main surface of the connection member (3) an underwear connection means (5) is present which is configured to fix the connection member (3) to a piece of underwear (12) and on the opposing main surface of the connection member (3) an absorbent member connection means (6) is present which is configured to fix the connection member (3) to the underside of an absorbent member (2, 2*a*).

19 Claims, 5 Drawing Sheets

(51) Int. Cl.
   *A61F 13/56*   (2006.01)
   *A61F 13/66*   (2006.01)
   *A61F 13/74*   (2006.01)
   *A61F 13/60*   (2006.01)
   *A61F 13/62*   (2006.01)
   *A61F 13/505*  (2006.01)

(52) U.S. Cl.
   CPC .......... *A61F 13/622* (2013.01); *A61F 13/665* (2013.01); *A61F 13/74* (2013.01); *A61F 13/505* (2013.01); *A61F 2013/16* (2013.01); *A61F 2013/5055* (2013.01)

(58) Field of Classification Search
   USPC ................ 604/385.14, 385.11, 389, 391
   See application file for complete search history.

(56) References Cited

U.S. PATENT DOCUMENTS

| | | | |
|---|---|---|---|
| 4,775,310 A | 10/1988 | Fischer | |
| 4,839,131 A | 6/1989 | Cloeren | |
| 4,894,060 A | 1/1990 | Nestegard | |
| 5,077,870 A | 1/1992 | Melbye et al. | |
| 5,415,650 A | 5/1995 | Sigl | |
| 5,613,964 A * | 3/1997 | Grenier | A61F 13/15211 604/358 |
| 5,778,457 A | 7/1998 | Conway | |
| 5,868,987 A | 2/1999 | Kampfer et al. | |
| 5,953,797 A | 9/1999 | Provost et al. | |
| 6,015,934 A * | 1/2000 | Lee | A61F 13/15747 604/358 |
| 6,075,179 A | 6/2000 | McCormack et al. | |
| 6,076,238 A | 6/2000 | Arsenault et al. | |
| 6,077,255 A | 6/2000 | Hunter et al. | |
| 6,106,922 A | 8/2000 | Cejka et al. | |
| 6,132,660 A | 10/2000 | Kampfer | |
| 6,171,425 B1 | 1/2001 | Nukina et al. | |
| 6,190,594 B1 | 2/2001 | Gorman et al. | |
| 6,190,758 B1 | 2/2001 | Stopper | |
| 6,280,427 B1 | 8/2001 | Maggiulli | |
| 6,280,428 B1 | 8/2001 | Lash et al. | |
| 6,287,665 B1 | 9/2001 | Hammer | |
| 6,358,234 B1 | 3/2002 | Terada et al. | |
| 6,368,097 B1 | 4/2002 | Miller et al. | |
| 6,558,602 B1 | 5/2003 | Melbye et al. | |
| 6,627,133 B1 | 9/2003 | Tuma | |
| 6,708,378 B2 | 3/2004 | Parellada et al. | |
| 6,767,492 B2 | 7/2004 | Norquist et al. | |
| 7,198,743 B2 | 4/2007 | Tuma | |
| 7,214,334 B2 | 5/2007 | Jens et al. | |
| 7,725,992 B2 | 6/2010 | Efremova et al. | |
| 2002/0026167 A1 | 2/2002 | Pompa | |
| 2003/0045852 A1 | 3/2003 | Essleburn | |
| 2004/0133179 A1 * | 7/2004 | Steger | A61F 13/476 604/385.04 |
| 2005/0090792 A1 | 4/2005 | Johnston | |
| 2011/0319856 A1 | 12/2011 | Drevik | |

FOREIGN PATENT DOCUMENTS

| | | |
|---|---|---|
| EP | 0 705 064 B1 | 3/1994 |
| EP | 0 539 504 B1 | 2/1997 |
| JP | 40-36391 | 12/1940 |
| JP | 49-28695 | 3/1974 |
| JP | 50-87791 | 7/1975 |
| JP | 10 024062 A | 1/1998 |
| WO | WO 95/29655 | 11/1995 |
| WO | WO 2011075809 A1 | 6/2011 |

* cited by examiner

SANITARY PRODUCT SYSTEM

FIELD OF THE INVENTION

The present invention refers to a sanitary product attachment means, comprising a connection member having a first major surface having an underwear connection means which is configured to fix the connection member to a piece of underwear or other clothing, and an opposing second major surface having an absorbent member connection means which is configured to fix the connection member to a major surface of an absorbent member. The invention is further directed to a method of fixing a sanitary product to a piece of underwear, to a sanitary product system comprising the sanitary product attachment means and absorbent member, and further to a method of exchanging a used absorbent member of the sanitary product system according to this invention. The present invention is also directed to use of the sanitary product attachment means to connect an absorbent member to a piece of underwear.

BACKGROUND

It is well known that absorbent members are provided with a pressure sensitive adhesive layer in order to fix the absorbent member, for example a diaper or a sanitary napkin, to a piece of underwear. The diapers, pads or panty-liners are partly or fully coated with the above mentioned adhesive and usually provided with a silicon paper liner or siliconized plastic pouches to protect the pad adhesive during the manufacturing process, storage and transportation. Those liners are removed at the point of use.

The use of adhesive, however, has various disadvantages and drawbacks. Adhesive-based fastening systems, for instance, may leave residue on the wearer's clothes, may stick to the wearer's hair and skin, can be moisture sensitive, and can be difficult to reposition without losing adhesive strength and other characteristics. Adhesives can also cause the products to stick to themselves and/or to other adjacent products. For example, when these pads are used, the adhesive coated pads are often folded, twisted or bent, leading to an adhesive to adhesive contact which results in almost permanent destruction of the absorbent pads, even before the pad is ever used.

In another typical application for adult incontinence, the pads are not adhesive coated and rely on insertion of the absorbent pad into mesh pants, i.e. elasticized underwear substitutes. This solution is not satisfactory because of the problems with disorientation during use.

To overcome those problems at least partly, U.S. Pat. No. 5,415,650 B describes the possibility to provide a sanitary napkin as well as a piece of undergarment with a cohesive-adhesive. This application also recites to provide the sanitary napkin with side wings which can be folded around the undergarment to improve the fixation of the sanitary napkin and prevent it from disorientation during use.

In U.S. Pat. No. 6,358,234 B1, a sanitary napkin with elastic side-flaps is recited so that movements of the wearer of the sanitary napkin can be compensated better and a part of the mechanical stress may be removed from the adhesive bond area.

From U.S. Pat. No. 6,077,255 B it is known to fix sanitary napkins by a hook and loop system, in other words by purely mechanical fixation means. Such fastening systems typically include a male component that is configured to engage a female component. The male component typically includes a backing material with a number of protruding hook elements. In conventional hook and loop fastening systems, the female component comprises a backing member having a plurality of loops that are engaged by the hook elements. For example, in one embodiment, the hook element may include a base, a shank, and an engaging means in the form of a hook, a cap, a spherical/hemispherical shape, a flat top, etc. Recently, microprotrusions have been used as the male component of a hook and loop mechanical fastening system. The microprotrusions, for instance, have a length of less than about 0.9 cm, such as from about 0.1 cm to about 0.001 cm. Such microprotrusions are capable of engaging most textile materials, in addition to loop materials, without the need of a specially shaped engaging means located at the top of the protrusions.

Mechanical fastening systems including microprotrusions are particularly well suited for use in feminine hygiene products. Such protrusions, for instance, are capable of engaging a wearer's underwear for maintaining the product in the proper position. The underwear becomes the female component in the mechanical fastening system. Unfortunately, however, some of these mechanical fasteners can damage the underwear through unwanted engagement. For example, the female component can be damaged in various ways including but not limited to pilling, snagging, pull-out, abrasion, distortion, wear, residue, and the like. Pilling, for instance, is the tendency of woven fabrics and knits, especially wools, nylons, and acrylics, to form surface nubs or bunches of fibers. Pilling is caused by loosely twisted yarns and winding and interlocking with each other. Fiber pull-out is especially problematic. Fiber pull-out occurs when the male component pulls on and releases fibers from the female component. Even when a single engagement of a component of the mechanical fastener system might produce minimal damage to the underwear or other female component of the mechanical fastener system, multiple engagement of the male component might produce significant damage in the female component of the mechanical fastener system. This multiple engagement damage is especially important when one of the components is durable (not disposable), like underwear, and the other component is disposable, like a feminine hygiene product.

From U.S. Pat. No. 7,725,992 B2 it is known to modify at least a portion of the male component protrusions or microprotrusions to reduce female component damage like abrasion or fiber pull-out caused by the protrusions. The manner in which the protrusions are modified can vary depending upon the particular application and the desired result. The surface-modified mechanical fastener is well suited to being used on an absorbent article such as a diaper, a training pant, a feminine hygiene product, an incontinence product, a wound care product, a medical garment, and the like. When used in a feminine hygiene product, for instance, the mechanical fastener is capable of holding the product in position by attaching to a user's clothing without damaging the clothing during single or multiple engagements of the mechanical fastener system.

It is also known in the prior art to use several layers of sanitary napkins in the form of a stack so that during use the absorbent members are removed subsequently in top-down direction. Such a construction is described in US2005/0090792 A1.

This solution has the drawback that the sanitary product is overall quite thick, which reduces the wearing comfort. On the other hand, if each individual absorbent member is made very thin to compensate the problems of wearing comfort, the absorbent capabilities and thus the security is reduced as well.

SUMMARY

The wide variety of technical solutions in the field of fixation of sanitary napkins to a piece of underwear have in common that a better fixation of the napkin is usually connected to a more complicated build-up of the fixation means of the napkin or sanitary pad respectively.

A further drawback of the above mentioned solutions is that safe securing of an absorbent article in the underwear cannot satisfyingly be achieved with untreated absorbent members, so that a fixation means is usually part of the absorbent article, such as a sanitary napkin. This makes the production of the absorbent article complicated and also expensive.

The object of the current invention is to provide an alternative fixation solution for sanitary napkins and other absorbent articles which is easy and cheaper to produce and easy to handle. Further, it shall combine reliable fixation of the absorbent article to a piece of underwear and good wearing comfort. The exchange of used articles should also be improved.

This object has been solved by a sanitary product attachment means comprising a connection member having a flexible base carrier, whereas on one main surface of the connection member an underwear connection means is present which is configured to fix the connection member to a piece of underwear and on the opposing main surface of the connection member an absorbent member connection means is present which is configured to fix the connection member to the underside of an absorbent member.

Hence, the inventive sanitary product allows the exchange of an absorbent member without exchanging the connection member. The connection member may remain fixed in the underwear, whereas the absorbent member can be exchanged several times if desired. Accordingly, the sanitary product system of the current invention can comprise a single connection member and a plurality of absorbent members.

According to the current invention, the absorbent member connection means may comprise and in particular consist of an adhesive coating and/or a mechanical fastener such as a hook or loop element, and the underwear connection means may comprise and in particular consist of an adhesive coating and/or a hook element. This allows the fixation of the connection member by different methods to the underwear and absorbent member. Accordingly, the connection member can be adapted to different types of underwear. This solution allows, for example, fixing the connection member to more delicate pieces of underwear by means of an adhesive instead of using a hook patch which might damage the underwear surface by roughening.

Regarding the adhesive, all types of adhesives can be used which are typically intended for a combination with sanitary products, for example a pressure sensitive adhesive, in particular based on an acrylic resin. Exemplary adhesives useful in the practice of the present invention include acrylic copolymer pressure sensitive adhesives, rubber based adhesives (e.g. those based on natural rubber, polyisobutylene, polybutadiene, butyl rubbers, styrene block copolymer rubbers, etc.), adhesives based on silicone polyureas or silicone polyoxamides, polyurethane type adhesives, and poly(vinyl ethyl ether) and copolymers or blends of these.

Regarding the hook element of a hook and loop fastening system, male fastening elements can be used such as those that are currently marketed, for example by Velcro USA Inc., 3M Co., Gottlieb Binder, Aplix, and Paiho.

The male fastening elements may be formed with a curved shape or they may be substantially upright stems that are deformed to include, for example, a head in the shape of mushroom. Some methods, which have varying degrees of versatility and complexity, are available to control the shape of loop-engaging heads. See, e.g., U.S. Pat. No. 3,192,589 (Pearson); U.S. Pat. No. 5,953,797 (Provost et al.); U.S. Pat. No. 6,132,660 (Kampfer); U.S. Pat. No. 6,558,602 (Melbye et al.) and U.S. Pat. No. 6,708,378 (Parellada et al.).

The male fastening elements include a thermoplastic backing with spaced-apart upstanding posts or stems with or without loop-engaging heads that have an overhang. The term "loop-engaging" as used herein relates to the ability of a male fastening element to be mechanically attached to a loop material. Generally, male fastening elements with loop-engaging heads have a head shape that is different from the shape of the stem. For example, the male fastening element may be in the shape of a mushroom (e.g., with a circular or oval head enlarged with respect to the stem), a hook, a palm-tree, a nail, a T, or a J. The loop-engageability of male fastening elements may be determined and defined by using standard woven, nonwoven, or knit materials. A region of male fastening elements with loop-engaging heads generally will provide, in combination with a loop material, at least one of a higher peel strength, higher dynamic shear strength, or higher dynamic friction than a region of stems without loop-engaging heads. Typically, male fastening elements that have loop-engaging heads have a maximum thickness dimension of up to about 1 mm, preferably up to about 750 μm, more preferably up to about 600 μm and, in particular, between about 200 and 550 μm.

The male mechanical fastener elements useful for practicing the present invention are typically made of a thermoplastic material. Suitable thermoplastic materials include polyolefin homopolymers such as polyethylene and polypropylene, copolymers of ethylene, propylene and/or butylene; copolymers containing ethylene such as ethylene vinyl acetate and ethylene acrylic acid; polyesters such as poly (ethylene terephthalate), polyethylene butyrate and polyethylene napthalate; polyamides such as poly(hexamethylene adipamide); polyurethanes; polycarbonates; poly(vinyl alcohol); ketones such as polyetheretherketone; polyphenylene sulfide; and mixtures thereof. Typically, the thermoplastic is a polyolefin (e.g., polyethylene, polypropylene, polybutylene, ethylene copolymers, propylene copolymers, butylene copolymers, and copolymers and blends of these materials).

In some embodiments, the mechanical fastener having a thermoplastic backing with upstanding posts can be made from a multilayer or multi-component melt stream of thermoplastic materials. This can result in posts formed at least partially from a different thermoplastic material than the one predominately forming the backing. Various configurations of upstanding posts made from a multilayer melt stream are shown in U.S. Pat. No. 6,106,922 (Cejka et al.), for example. A multilayer or multi-component melt stream can be formed by any conventional method. A multilayer melt stream can be formed by a multilayer feedblock, such as that shown in U.S. Pat. No. 4,839,131 (Cloeren). A multicomponent melt stream having domains or regions with different components could also be used. Useful multicomponent melt streams could be formed by use of inclusion co-extrusion die or other known methods (e.g., that shown in U.S. Pat. No. 6,767,492 (Norquist et al.).

In the mechanical fastener useful for practicing the present disclosure, the thermoplastic backing and the upstanding posts are typically integral (that is, formed at the same time as a unit, unitary). The thermoplastic backing is typically in the form of a sheet or web that may have an essentially uniform thickness with the spaced-apart upstanding posts or stems directly attached to the thermoplastic backing. The thermoplastic backing sheet typically is in the form of a continuous film, wherein "continuous" refers to having no holes in the film. Upstanding posts on a backing can be made, for example, by conventional extrusion through a die and cast molding techniques. In some embodiments, a thermoplastic material is fed onto a continuously moving mold surface with cavities having the inverse shape of the upstanding posts. The thermoplastic material can be passed between a nip formed by two rolls or a nip between a die face and roll surface, with at least one of the rolls having the cavities (i.e., at least one of the rolls is a tool roll). The cavities may be in the inverse shape of a capped post having a loop-engaging head or may be in the inverse shape of a post without loop-engaging heads (e.g., a precursor to a fastening element). In the invention disclosed herein, the term "posts" is meant to include posts with or without loop-engaging heads, depending on the embodiment. Pressure provided by the nip forces the resin into the cavities. In some embodiments, a vacuum can be used to evacuate the cavities for easier filling of the cavities. The nip is typically sufficiently wide such that a coherent backing is formed over the cavities. The mold surface and cavities can optionally be air or water cooled before stripping the integrally formed backing and upstanding posts from the mold surface such as by a stripper roll.

Suitable tool rolls can be made, for example, by drilling (e.g., by electron beam) a series of holes having the inverse shape of the upstanding posts into the cylindrical face of a metal mold or sleeve. Other suitable tool rolls include those formed from a series of plates defining a plurality of post-forming cavities about its periphery such as those described, for example, in U.S. Pat. No. 4,775,310 (Fischer). Cavities may be formed in the plates by drilling or photoresist technology, for example. Still other suitable tool rolls may include wire-wrapped rolls, which are disclosed along with their method of manufacturing, for example, in U.S. Pat. No. 6,190,594 (Gorman et al.). The exposed surface of the mold, sleeve, plate, or wire may be coated to impart surface properties such as increased wear resistance, controlled release characteristics, and controlled surface roughness. The coating, if present, is preferably selected so that the adhesion of the thermoplastic material to the tool roll is less than the cohesion of the thermoplastic material at the time of the removal of the thermoplastic backing from the tool roll.

Another exemplary method for forming a thermoplastic backing with upstanding posts or stems includes using a flexible mold belt defining an array of upstanding post-shaped cavities as described in U.S. Pat. No. 7,214,334 (Jens et al.). The mold belt is trained about first and second rolls, and a source of molten thermoplastic material is arranged to deliver the thermoplastic to the mold belt. The apparatus is constructed to force the plastic resin into the upstanding post-shaped cavities of the belt under pressure in a gap to mold the array of upstanding posts while forming the thermoplastic web layer. Yet other useful methods for forming a thermoplastic backing with upstanding posts or stems can be found in U.S. Pat. No. 6,287,665 (Hammer), U.S. Pat. No. 7,198,743 (Tuma), and U.S. Pat. No. 6,627,133 (Tuma).

If the posts formed upon exiting the cavities do not have loop-engaging heads, loop-engaging heads could be subsequently formed into hooks by a capping method as described in U.S. Pat. No. 5,077,870 (Melbye et al.), the disclosure of which is incorporated herein by reference in its entirety. Typically, the capping method includes deforming the distal tip portions of the hook elements using heat and/or pressure to form caps. The heat and pressure, if both are used, could be applied sequentially or at the same time.

A variety of methods are useful for deforming the distal tips of the spaced-apart upstanding posts. The caps that are formed after the deformation are larger in area than the cross-sectional area of the bases. A ratio of a width dimension of the formed cap to the post measured at the base is typically at least 1.5:1 or 3:1 and may be up to 5:1 or greater. The capped posts are typically shorter than the posts before deformation. In some embodiments, the capped posts have a height (above the backing) of at least 0.025 mm, 0.05 mm, or 0.1 mm and, in some embodiments, up to 2 mm, 1.5 mm, 1 mm, or 0.5 mm.

In some embodiments, deforming comprises contacting the distal tips with a heated surface. The heated surface may be a flat surface or a textured surface such as that disclosed in U.S. Pat. No. 6,708,378 (Parellada et al.) or U.S. Pat. No. 5,868,987 (Kampfer et al.). In some embodiments, wherein the thermoplastic backing with spaced-apart upstanding posts is a web of indefinite length, the deforming comprises moving the web in a first direction through a nip having a heated surface member and an opposing surface member such that the heated surface member contacts the distal tips. In these embodiments, the heated surface may be, for example, a capping roll. In some embodiments, the surfaces used to contact the distal tips may not be heated. In these embodiments, the deformation is carried out with pressure and without heating.

In some embodiments, the heated surface may be a heated roll opposite a curved support surface forming a variable nip having a variable nip length as described, for example, in U.S. Pat. No. 6,368,097 (Miller et al.). The curved support surface may curve in the direction of the heated roll, and the heated roll may include a feeding mechanism for feeding the thermoplastic backing with spaced-apart, upstanding posts through the variable nip to compressively engage the web between the heated roll and the support surface.

In embodiments wherein deforming comprises heating the distal tips of the upstanding posts, the heating is typically carried out below a melt temperature of the distal tips. When the thermoplastic material used to form the upstanding posts is a copolymer (e.g., copolymers of ethylene and propylene), the distal tips may have more than one melt temperature. In these embodiments, "below a melt temperature of the distal tips" means below at least one of the melt temperatures. Heating at a temperature below a melt temperature of the thermoplastic material in the distal tips is useful for preventing the caps upon forming from fusing together so that stretching the thermoplastic backing can readily separate the at least some caps from the at least one adjacent cap.

Another useful method for forming upstanding posts (e.g., with loop-engaging heads) on a backing is profile extrusion described, for example, in U.S. Pat. No. 4,894,060 (Nestegard), which is incorporated herein by reference in its entirety. Typically, in this method a thermoplastic flow stream is passed through a patterned die lip (e.g., cut by electron discharge machining) to form a web having down-web ridges, slicing the ridges, and stretching the web to form separated projections. The ridges may form hook precursors and exhibit the cross-sectional shape of upstanding posts (e.g., with loop-engaging heads) to be formed. The ridges are transversely sliced at spaced locations along the extension of the ridges to form discrete portions of the ridges having lengths in the direction of the ridges essentially corresponding to the length of the upstanding posts to be formed.

In addition to the continuous methods described above, it is also envisioned that thermoplastic backings having spaced-apart, upstanding posts can be prepared using batch processes (e.g., single piece injection molding). The thermoplastic backing may have any suitable dimension, but length (L) and width (W) dimensions of at least 10 cm may be useful.

The spaced-apart upstanding posts or stems, which may be made, for example, by any of the methods described above, may have a variety of cross-sectional shapes. For example, the cross-sectional shape of the post may be a polygon (e.g., square, rectangle, hexagon, or pentagon), which may be a regular polygon or not, or the cross-sectional shape of the post may be curved (e.g., round or elliptical).

In some embodiments, the upstanding posts or stems, which may be made, for example, by any of the methods described above, may have a shape that tapers, for example, from the base portion to the distal tip. The base portion may have a larger width dimension than the distal tip, which may facilitate the removal of the post from the mold surface in the methods described above. Again, in these embodiments where the posts have a shape that tapers, the aspect ratio described above is the height over the largest width dimension, which may be at the base of the post.

In some embodiments, the thermoplastic backing has stretch-induced molecular orientation, for example, when the thermoplastic backing with upstanding posts is prepared by profile extrusion or in other cases where the thermoplastic backing is stretched after formation of the upstanding posts. In other embodiments, the thermoplastic backing is not provided with macroscopic stretch-induced molecular orientation.

For the mechanical fastener according to or useful in the invention of the present disclosure in any of its various embodiments, the thermoplastic backing sheet may have a variety of thicknesses depending on the desired application. For example, the thickness of the thermoplastic backing sheet may be up to about 750, 500, 400, 250, or 150 micrometers, depending on the desired application. In some embodiments, the thickness of the backing is at least about 5, 10, 30, 50, 75, or 100 micrometers, depending on the desired application. In some embodiments, the thickness of the thermoplastic backing sheet is in a range from 10 to about 225 micrometers, from about 30 to about 200 micrometers, or from about 50 to about 150 micrometers. The thermoplastic backing sheet may have an essentially uniform cross-section, or the thermoplastic backing sheet may have additional structure (e.g., grooves) beyond what is provided by the upstanding posts which may be imparted, for example, by at least one of the forming rolls described above. However, in some embodiments, the thermoplastic backing sheet has a smooth surface aside from the upstanding posts (e.g., in first and second upstanding elements). In some embodiments, the thermoplastic backing sheet is essentially flat.

In some embodiments, the spaced-apart posts or stems, upon being formed on a backing, for example, by any of the methods described above, have a maximum height (above the backing) of up to 3 millimeters (mm), 1.5 mm, 1 mm, or 0.5 mm and, in some embodiments a minimum height of at least 0.05 mm, 0.075 mm, 0.1 mm, or 0.2 mm. In some embodiments, the posts have aspect ratio (that is, a ratio of height over a width dimension) of at least about 2:1, 3:1, or 4:1. The aspect ratio may be, in some embodiments, up to 10:1. The posts may have a cross-section with a maximum width dimension of up to 1 (in some embodiments, up to 0.75, 0.5, or 0.45) mm. In some embodiments, the posts have a cross-section with a width dimension between 10 µm and 350 µm. As described above, the cross-sectional dimensions among different posts can be different. In some embodiments, the maximum width dimension of some posts may be up to twice the maximum width dimension of other posts. The term "width dimension" should be understood to include the diameter of a post with a circular cross-section. When the post has more than one width dimension (e.g., in a rectangular or elliptical cross-section shaped post), the aspect ratio described herein is the height over the largest width dimension.

Some hook strips which may be useful precursors for the male fastener element according to the present disclosure are commercially available, e.g., from 3M Company, St. Paul, under the trade designations "CS-600" or "CS-1010".

Regarding the loop element of a hook and loop mechanical fastening system, in some embodiments, the female fastening elements may be in the form of a loop patch. Loop patches can be made from any suitable material that interlocks with a corresponding hook fastening element. In some embodiments, the loop fastening elements are typically formed from knitted, woven, or non-woven fabrics. For example, the mechanical fastening patches may include fiber loops projecting from a knitted, woven, or non-woven backing or may be extrusion-bonded, adhesive-bonded, and/or sonically-bonded fiber loops. Suitable commercially available mechanical fastening patches include knitted and extrusion-bonded loop materials from 3M Company, St. Paul, Minn.

Examples of loop patches which may be applied to a target area to provide an exposed fibrous material, are disclosed, for example, in U.S. Pat. No. 5,389,416 (Mody et al.), EP 0,341,993 (Gorman et al.) and EP 0,539,504 (Becker et al.). In some embodiments, the target area, such as the backsheet of a personal hygiene article or the absorbent member connection means on an absorbent article connection member, comprises a woven or nonwoven fibrous layer which is capable of interacting directly with the male mechanical fastening element. Examples of such back sheets are disclosed, for example, in U.S. Pat. No. 6,190,758 (Stopper) and U.S. Pat. No. 6,075,179 (McCormack et al.).

In some embodiments, the thermoplastic backing of the mechanical fastening element is not joined to a carrier, at least when it is initially formed. In other embodiments, a second surface of the thermoplastic backing (i.e., the surface opposite the first surface from which the spaced-apart, upstanding posts or loops project) is joined to a carrier. The thermoplastic backing may be joined to a carrier, for example, by lamination (e.g., extrusion lamination), adhesives (e.g., pressure sensitive adhesives), or other bonding methods (e.g., ultrasonic bonding, compression bonding, or surface bonding). The thermoplastic backing may be joined to a carrier during the formation of the thermoplastic backing with upstanding posts or loops.

The carrier may be continuous (i.e., without any through-penetrating holes) or discontinuous (e.g. comprising through-penetrating perforations or pores). The carrier may comprise a variety of suitable materials including woven webs, non-woven webs (e.g., spunbond webs, spunlaced webs, airlaid webs, meltblown web, and bonded carded webs), textiles, plastic films (e.g., single- or multilayered films, coextruded films, laterally laminated films, or films comprising foam layers), and combinations thereof. In some embodiments, the carrier is a fibrous material (e.g., a woven, nonwoven, or knit material). In some embodiments, the carrier comprises multiple layers of nonwoven materials with, for example, at least one layer of a meltblown nonwoven and at least one layer of a spunbonded nonwoven, or any other suitable combination of nonwoven materials. For example, the carrier may be a spunbond-meltbond-spunbond, spunbond-spunbond, or spunbond-spunbond-spunbond multilayer material. Or, the carrier may be a composite web comprising a nonwoven layer and a dense film layer.

The term "nonwoven" when referring to a sheet or web means having a structure of individual fibers or threads which are interlaid, but not in an identifiable manner as in a knitted fabric. Nonwoven fabrics or webs can be formed from various processes such as meltblowing processes, spunbonding processes, spunlacing processes, and bonded carded web processes.

Fibrous materials that provide useful carriers may be made of natural fibers (e.g., wood or cotton fibers), synthetic fibers (e.g., thermoplastic fibers), or a combination of natural and synthetic fibers. Exemplary materials for forming thermoplastic fibers include polyolefins (e.g., polyethylene, polypropylene, polybutylene, ethylene copolymers, propylene copolymers, butylene copolymers, and copolymers and blends of these polymers), polyesters, and polyamides. The fibers may also be multi-component fibers, for example, having a core of one thermoplastic material and a sheath of another thermoplastic material.

Useful carriers may have any suitable basis weight or thickness that is desired for a particular application. For a fibrous carrier, the basis weight may range, e.g., from at least about 20, 30, or 40 grams per square meter, up to about 400, 200, or 100 grams per square meter. The carrier may be up to about 5 mm, about 2 mm, or about 1 mm in thickness and/or at least about 0.1, about 0.2, or about 0.5 mm in thickness.

Although a hook strip of a hook-and-loop fastener is typically sold with a cooperating loop strip, the hook strip can be used by itself to become releasably fastened to fabrics that can be easily penetrated by the hooks. Mushroom-type hook strips are particularly suited for such use. Mushroom-type mechanical fasteners are sometimes designed so that two hook strips can be used to fasten two articles together by adhering each strip to one of the articles and then interengaging the two strips. Such a mushroom-type mechanical fastener is shown in U.S. Pat. No. 3,192,589, in which the fastener is called "hermaphroditic", because its headed studs have both male and female characteristics when intermeshed. Such interengaging articles are also described in U.S. Pat. No. 3,408,705 and U.S. Pat. No. 6,076,238. Other mushroom-type mechanical fasteners which can be used as hook and/or loop element are described in EP 549 705 B1 and EP 705 064 B1.

According to a preferred embodiment of the current invention, the adhesion of the underwear connection means to a piece of underwear is higher than the adhesion of the absorbent member connection means to a major surface of an absorbent member. For example the adhesion of the underwear connection means adhesive to an underwear material is higher than the adhesion of the absorbent member connection means adhesive to an absorbent member material.

This embodiment has the advantage that the exchange of the absorbent member without removing the connection member from the underwear is much easier and better to control. As in many cases the connection member is in the form of rectangular-shaped flat element of smaller size than the absorbent member, it may be difficult to grab the edge of the connection member under the napkin when the system is fixed into the underwear. The different bonding strength of the fasteners used on both sides of the connection member currently allows the user to remove the absorbent member just by pulling the used absorbent member out of the underwear. The weaker adhesion of the absorbent member connection means to the absorbent member compared to the adhesion between the connection member and the underwear ensures that a connection member stays in the underwear.

Adhesives which are capable to be used in this embodiment can be formulated by comparative adhesion tests to typical underwear and absorbent member surfaces. The tack of the adhesive to the before mentioned surfaces can be influenced as known by the skilled person by the type of polymer latex, adhesion promoters like tackifiers, softeners or filler substances and so on.

Another embodiment of this invention is characterised in that the absorbent member connection means comprises further layers of the flexible base carrier arranged in a stack and provided with an adhesive coating on at least one of their main surfaces, the adhesive coating being preferably identical to the absorbent member connection means adhesive. Also, the material of the further layers of the flexible base carrier may be identical to the material of that the base carrier, which is provided with the underwear connection means.

The stack-like arrangement is advantageous because the adhesive strength of a pressure sensitive adhesive is typically reduced after the adhesion bond has been breached. In other words, removing the used absorbent member from the connection member strongly weakens the adhesive strength of the absorbent member connection means so that sufficient fixation of a new absorbent member may not always be guaranteed. The current embodiment allows removing the upper adhesive layer from the stack together with the used absorbent member to reveal a fresh and unused adhesive surface for best bonding of the new absorbent member attached thereto.

Although the amount of further layers is in principal not limited, the wearing comfort is reduced if the number of further layers is too high, because the connection member is stiffened. It is therefore advantageous to use 1 to 8 further layers, in particular 2 to 6 further layers.

In the context of the before mentioned embodiments, it is further preferred that one (or more) edge(s) of the flexible base carriers contains a fingerlift area that is free from the adhesive coating. The fingerlift area makes it easier for the user to grip the top layer from the stack of base carriers together with the used absorbent member for exchanging it.

To ensure that only the top layer of the stack of base carriers is removed together with the used absorbent member, and to prevent splitting of the stack between other layers which would result in a loss of some of the layers of the base carrier, the layers of the base carrier may be arranged with a lateral offset in the stack. This offset is preferably oriented in a stepwise fashion towards the underwear connection means, in particular on the edge of the fingerlift area.

Although the further layers of the base carrier may be provided on both main surfaces with an adhesive coating, it is preferred that the adhesive coating is provided on one of the main surfaces, whereas at least a portion of the opposing main surface contains a LAB coating such as a silicone or is otherwise modified by corona-treating, priming, sputtering, plasma-treating or otherwise reducing the adhesion to the next layer in the stack. This allows an easier separation between the layers.

According to an another embodiment of the sanitary product according to the current invention, the absorbent member connection means comprises a hook element and the underwear connection means comprises an adhesive layer or a hook element, the adhesive layer being in particular a pressure sensitive adhesive layer.

According to this embodiment, the connection between the absorbent member and the connection member is achieved by a hook element which interacts with an untreated, non-woven surface of the absorbent member. Untreated means in that context, that the surface is not provided with a loop element or the like. This has the advantage of reducing the cost of manufacturing the absorbent member, since no hook or adhesive needs to be applied to the underside of the absorbent member to fix it to the underwear. Of course, the absorbent member may also be provided with a corresponding hook or loop element to interact with the hook element of the connection member.

According to a preferred embodiment of the before mentioned sanitary product, the adhesion of the underwear connection means to an underwear material is higher than the adhesion of the absorbent member connection means, i.e. the hook element, to a major surface of the absorbent member material.

Such a preferred embodiment ensures that during removal of the used absorbent member, the bond between the connection member and the absorbent member is breached easier so that the connection member remains in the underwear. This effect can be achieved for example by the size of the hook element compared to the adhesive strength of the underwear connection means as well as by choosing the type of hooks which has the desired bonding strength to the absorbent member material or surface, respectively. Other ways to achieve this may for example include varying the height, shape density of the hooks, arranging hook patches and/or selection of the adhesive.

According to another sanitary product system of this invention, the absorbent member connection means comprises or consists of a loop element and the underwear connection means comprises or consists of a heat-activated adhesive coating, in particular a hot-melt adhesive coating, so that the combination of the connection member adhered to a piece of underwear is wash-resistant. In such an embodiment, a corresponding absorbent member needs to be provided with a hook element.

This embodiment allows providing a piece of underwear permanently with a connection member. Alternatively, the sanitary product attachment means can be sewn into the underwear. The absorbent member connection means is chosen to be a loop element in order to avoid sticking of the connection member to other parts of the underwear or other pieces of clothing in the washing machine during the washing process, which would probably be the case when a hook element would be chosen.

Further, the heat-activated adhesive provides a strong bond between the connection member and the piece of underwear so that during the exchange procedure of the absorbent member, the bond between the connection member and the absorbent member is usually breached while leaving the bond between the connection member and the piece of underwear intact.

The hook, loop or adhesive fastening means may be applied to a base carrier layer. According to a preferred embodiment of the sanitary product system, the material of the base carrier is chosen from polymeric films, in particular polyethylene, polypropylene, polystyrene, polyester, preferably polyethylene terephthalate, polyurethane, or mixtures thereof as well as non-wovens or meshes. For some applications, the base carrier could instead be paper or a nonwoven film. Although for each layer a different material could be chosen, it is preferred that the same material is selected for all layers of the base carrier. Although the current invention is not limited to the before mentioned materials, these are particularly useful as they combine sufficient flexibility for good wearing comfort with a sufficient strength to not suffer distortion during the use, especially during the exchange of a used absorbent member.

The thickness of each layer of the base carrier may be in the range of 5 to 100 μm, preferably from 10 to 50 μm to improve flexibility and comfort. This applies also to those embodiments in which only one layer of the base carrier is present.

In some embodiments of the sanitary product attachment means according to the current invention, the connection member comprises wings on opposing edges, which are provided with a hook element or an adhesive coating, in particular at the longitudinal sides of the connection member. The use of such wings or flaps further increases the bond strength between the connection member and the piece of underwear.

Although the adhesive layers and/or the hook and/or loop elements can be applied in a continuous way in any application cases described above, it may be preferred that the adhesive layer, the hook and/or the loop element is separated into two or more regions, in particular in the form of several stripes, squares, oval or round dots, grids, or combinations thereof. The regions may be discontinuous or may connect with each other, such as in a pattern.

In order to protect the outermost adhesive layer of the connection member according to the current invention, the adhesive layer may be covered by a release liner, like siliconized paper, a siliconized polymeric film or the like which is removed prior to application of the connection member to the underwear and/or to the absorbent member.

A further object of this invention is a sanitary product system comprising a sanitary product attachment means according to this invention and at least one absorbent member. As set out before, the advantage of the sanitary product attachment means of this invention is that it may remain in the underwear while only the absorbent member may be changed.

Regarding the absorbent member, the current invention is not limited to the type of absorbent member used in combination with the sanitary product attachment means, which means that in principal all types of absorbent members used for sanitary products may be part of the sanitary product system of this invention. Examples are a diaper, a sanitary napkin or pad, a panty liner, an incontinence pad, etc. It is however conceivable for most embodiments of this invention that the absorbent member does not comprise any connection means like adhesive layers, hook or loop elements.

The absorbent member typically comprises an absorbent core to absorb fluids and is generally compressible, conformable and non-irritating to the user's skin. It may comprise any material used in the art for such purpose. Non-limiting examples include natural materials such as comminuted wood pulp which is generally referred to as airfelt, creped cellulose wadding, hydrogel-forming polymer gelling agents, modified cross-linked cellulose fibres, absorbent foams, absorbent sponges, synthetic staple fibres, polymeric fibres, peat moss, or any equivalent material or combinations thereof.

The polymeric gelling agents mentioned above may also be referred to as "absorbent gelling materials", "super absorbent materials", or "super absorbent polymers". These agents imbibe upon contact with liquids such as water or other body liquids and thereby form hydrogels. In this manner, liquids discharged into the absorbent core can be acquired and held by the polymeric gelling agent, thereby providing the articles herein with enhanced absorbent capacity and/or improved liquid retention performance. The polymeric gelling agent which is employed in the absorbent core will generally comprise particles of the substantially water-insoluble, slightly cross-linked, partially mutualised, hydrogel-forming polymer material. The polymeric gelling agent can be in many forms, including the form of pellets, flakes or fibres. The core is typically fixed between a fluid pervious top layer that faces the body and a fluid impervious backsheet that faces the underwear.

The current invention is further directed to a method of fixing a sanitary product to a piece of underwear or other clothing, the method comprising the steps of fixing the connection member to the underwear with the underwear connection means and fixing the absorbent member to the connection member with the absorbent member connection means.

A further object of this invention is a method of exchanging a used absorbent member of a sanitary product system according to this invention which has been fixed to the piece of underwear, the method comprising the steps of unfixing the used absorbent member from the connection member, in particular while leaving the connection member connected to the piece of underwear, and fixing a new absorbent member to the connection member.

The current invention is also directed to a method of exchanging a used absorbent member of a sanitary product system of this invention which has been fixed to the piece of underwear, the method comprising the steps of peeling the used absorbent member together with the adjacent base carrier from the stack, in particular by grabbing the fingerlift area of this base carrier, to reveal a fresh adhesive coating on the connection member and bonding a new absorbent member to the fresh, i.e. unused adhesive coating.

In the context of the before mentioned method, the steps may be repeated at least once, preferably until all base carriers have been used to fix an absorbent member to the connection member.

The current invention is further directed to the use of a sanitary product attachment means of this invention for connecting an absorbent member to a piece of underwear.

It is also conceivable to arrange adhesive and hook elements side-by-side, which may help to increase the bonding reliability for example in critical applications. Also, additional connection means may be conceivable.

In the following part, the current invention is explained in more detail with the examples given in the figures.

DETAILED DESCRIPTION

Figure 1:
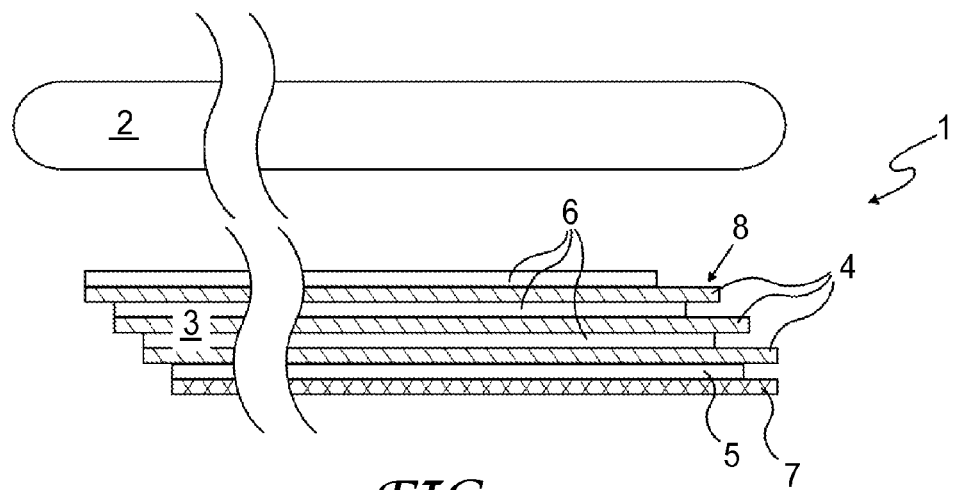
FIG. 1 is a first embodiment of the inventive sanitary product system with a stack-wise arrangement of the connection member in cross-sectional view.

In FIG. 1, a first embodiment of a sanitary product system 1 is illustrated in frontal sectional view. The sanitary product system 1 comprises one absorbent member 2 and a separate connection member 3, which are not displayed in FIG. 1 true to scale. The absorbent member 2 is an untreated sanitary napkin, i.e. the napkin is not provided with any adhesive or other mechanical fixation means.

The connection member 3 comprises a plurality of flexible base carriers 4 made from a 50 μm polyethylene-terephthalate (PET) foil from which the lower base carrier 4 is covered on one side with a high-tack pressure sensitive adhesive to represent an underwear connection means 5. Alternately, the underwear connection means 5 could be a hook fastener. The opposite main surface of each base carrier 4 is covered with a lower tack pressure sensitive adhesive which represents an absorbent member connection means 6. The opposing surface of each layer of the base carrier 4 is tack-reducing modified by a corona treatment, with the exception of the lower base carrier 4.

The underwear connection means 5 is covered with a release liner 7 made from siliconized paper, which is removed prior to use. Also the outermost adhesive layer of the connection means 6 may be covered with a release liner 7.

At an edge of each layer of the base carrier 4, an area is left free from the adhesive coating, thus forming a fingerlift area 8 in order to ease the removal of each of these layers.

The layers of the base carrier 4 are arranged on top of each other in a stack-like manner in such a way that a layer of fresh adhesive 6 is exposed each time the top layer is removed until only the lower base carrier 4 is left.

As recognizable in FIG. 1, the layers of the base carrier 4 may be arranged in the stack with a lateral offset in a step-wise fashion towards the underwear connection means 5 on the edge of the fingerlift area 8. This lateral offset ensures that during exchange of a used absorbent member 2 by a fresh one, only the adjacent base carrier 4 is removed from the top of the stack together with the used absorbent member 2.

Figure 2:
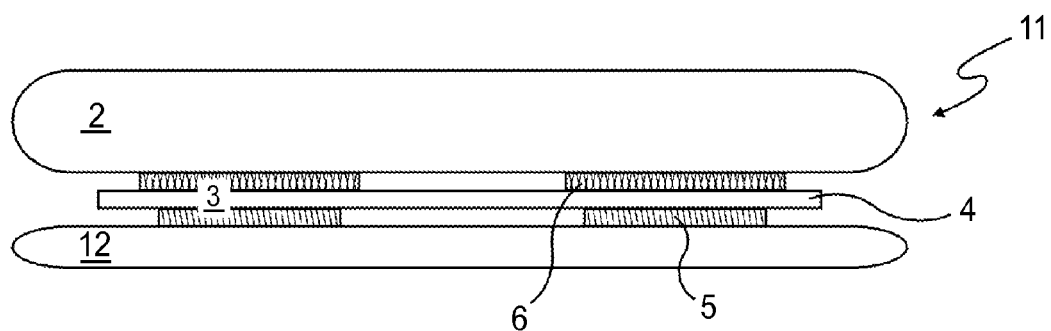
FIG. 2 is a second embodiment of an inventive sanitary product system in cross-sectional view.
Figure 3:
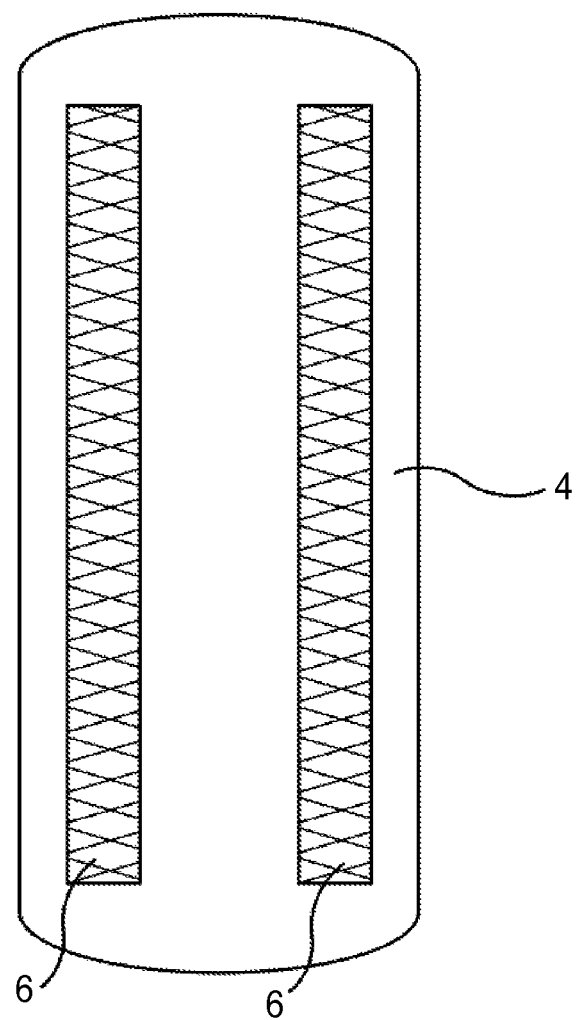
FIG. 3 is the embodiment of an inventive sanitary product system in top view.

In FIG. 2, an alternative embodiment of the sanitary product system 11 of the current invention is shown in frontal sectional view. FIG. 3 displays the same embodiment in top view but with the absorbent member 2 removed to show the top of the connection member. The sanitary product system 11 comprises an absorbent member 2 in form of an adhesive-free sanitary napkin and a connection member 3.

The absorbent member 2 is the same as set out above. The connection member 3 comprises a flexible base carrier 4 which is attached to a piece of underwear 12 by an underwear connection means 5, which consists of two stripes of a pressure sensitive adhesive. Alternatively, the underwear connection means 5 can be one or more strips of a hook fastener. On the opposing main surface, the base carrier 4 is provided with an absorbent member connection means 6 in the form of two stripes of hook elements which interact with the surface of the absorbent member 2.

The sizes and bond strength of the underwear connection means 5 and the absorbent member connection means 6 are matched to one another in such a way that during an exchange of the absorbent member 2 by pulling, only the bond between the absorbent member connection means 6 and the absorbent member 2 is breached.

Figure 4:
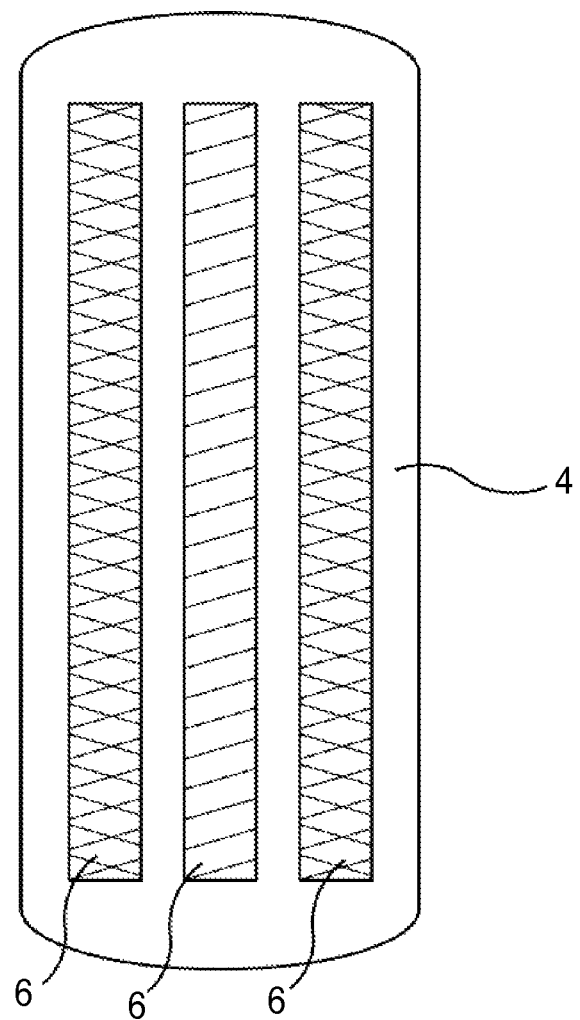
FIG. 4 is a modified version of the sanitary product system according to FIGS. 2 and 3 in top view.

FIG. 4 shows an alternative set-up of the embodiment of FIG. 3 with three mostly parallel absorbent member connection means 6, from which the outer absorbent member connection means 6 are represented by two stripes of a pressure sensitive adhesive, between which a single strip of a hook element is present.

Figure 5:
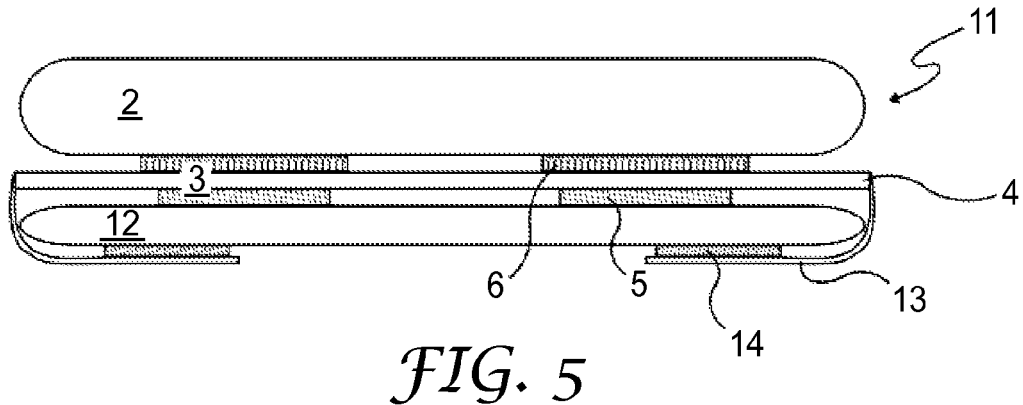
FIG. 5 is a modified version of the sanitary product system according to FIG. 2 in cross-sectional view.

In FIG. 5, a modification of the embodiment according to FIG. 2 is shown in frontal sectional view. The main difference to the embodiment of FIG. 2 is that the connection member 3 is provided on both its long sides with wings 13. Each of the wings 13 is provided with an adhesive coating 14 in order to fix the end of each wing 13 to the bottom side of the piece of underwear 12. Alternately, hook fasteners can be used in place of the adhesive coating on the wings.

Figure 6:
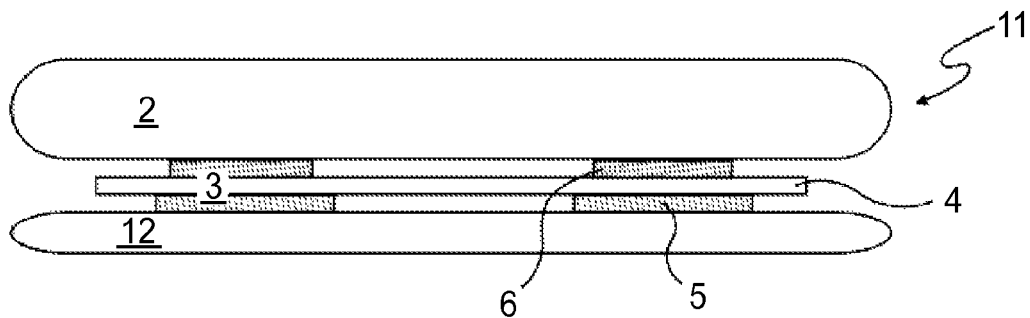
FIG. 6 is a second alternative of the sanitary product system according to FIG. 2 in cross-sectional view.

In FIG. 6, another alternative to the example as displayed in FIG. 2 is shown in frontal sectional view. According to this embodiment, the absorbent member connection means 6 is represented by stripes of a pressure sensitive adhesive coating. Alternately, both the absorbent member connection means 6 and the underwear connection means 5 could include one or more strips of hook fasteners instead of or in addition to the adhesive stripes. The adhesion strength of the underwear connection means 5 to a piece of underwear 12 is higher than the adhesion strength of the absorbent member connection means 6 to a major surface of the absorbent member 2, so that by applying a pull force to the absorbent member 2, the bond between the absorbent member connection means 6 and the absorbent member 2 is breached.

Figure 7:
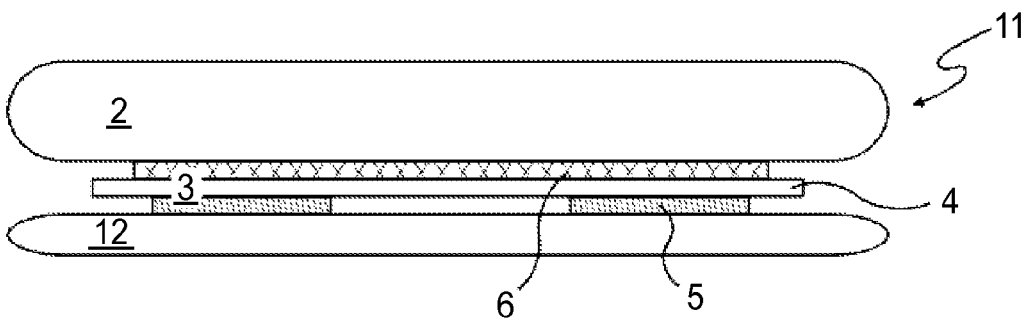
FIG. 7 is a third alternative of a sanitary product system according to FIG. 2 in cross-sectional view.

FIG. 7 shows an alternative set-up of the sanitary product system 11 of FIG. 2 in frontal sectional view. In that embodiment, the absorbent member connection means 6 is a single continuous hook element patch.

Figure 8:
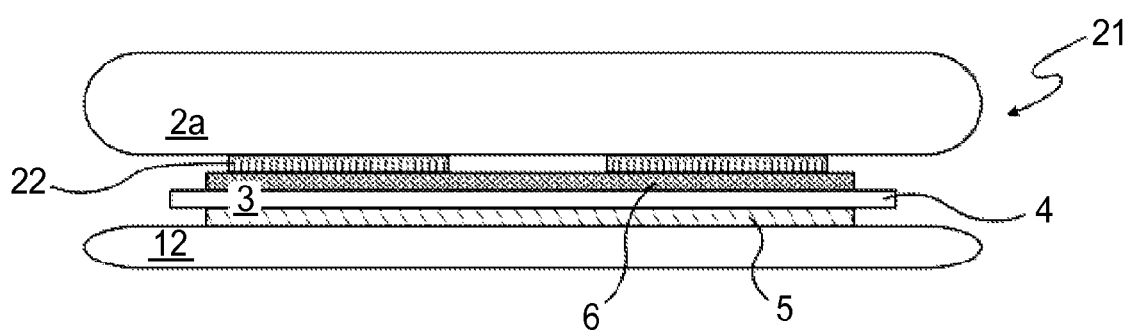
FIG. 8 is a third embodiment of the inventive sanitary product system in cross-sectional view.

FIG. 8 illustrates a third embodiment of a sanitary product system 21 according to the current invention in frontal sectional view. In this embodiment the base carrier 4 of the connection member 3 is attached with a hot melt adhesive as underwear connection means 5 to the piece of underwear 12. This is achieved for example by ironing the connection member 3 to the piece of underwear 12.

The absorbent member connection means 6 is represented in this case by a continuous loop element which may interact with a hook element 22 of an alternative absorbent member 2a. In other words, in this example the absorbent member 2a is provided with a part of an attachment means, namely a hook element.

The hot melt adhesive of the sanitary product system 21 allows washing of the piece of underwear 12 in one piece with the connection member 3. The absorbent member connection means 6 in the form of a loop element ensures that during washing, neither the piece of underwear 12 nor other parts of clothing in the washing machine are damaged. Alternately, the connection member 3 may be sewn into the underwear 12 instead of using a hot-melt adhesive.

The invention claimed is:

1. A sanitary product attachment means comprising a connection member having a flexible base carrier, wherein on one main surface of the connection member an underwear connection means is present which is configured to fix the connection member to a piece of underwear and on the opposing main surface of the connection member an absorbent member connection means is present which is configured to fix the connection member to the underside of an absorbent member, and wherein the underwear connection means comprises an adhesive coating and/or a hook element thereon;

wherein the underwear connection means is disposed on a main surface of the flexible base carrier and the absorbent member connection means is disposed on an opposing main surface of the flexible base carrier, and further wherein the adhesion of the underwear connection means to a piece of underwear is higher than the adhesion of the absorbent member connection means to a major surface of an absorbent member.

2. The sanitary product according to claim 1, characterized in that absorbent member connection means comprises an adhesive coating.

3. The sanitary product according to claim 2, characterized in that the absorbent member connection means comprises further layers of the flexible base carrier arranged in a stack and provided with an adhesive coating on at least one of their main surfaces, whereas 1 to 8 further layers are present.

4. The sanitary product according to claim 3, characterized in that adjacent one edge of the flexible base carriers, a fingerlift area is defined on the major side of the base carrier coated with adhesive and which is free from the adhesive coating.

5. The sanitary product according to claim 3, characterized in that the flexible base carriers are arranged with a lateral offset preferably in a step-wise fashion towards the underwear connection means.

6. The sanitary product according to claim 3, characterized in that the further layers of the flexible base carrier are provided with the adhesive coating on at least a portion of their main surfaces, whereas the opposing main surface is modified to reduce tack.

7. The sanitary product according to claim 2, characterized in that the adhesive layer, the hook and/or the loop element is separated into two or more regions, in particular in the form of several stripes, squares, oval or round dots, grids, or combinations thereof.

8. The sanitary product according to claim 2, characterized in that, the outermost adhesive layers are covered by a release liner.

9. The sanitary product according to claim 1, characterized in that the absorbent member connection means comprises a hook element and the underwear connection means comprises an adhesive layer and/or a hook element provided thereon.

10. The sanitary product according to claim 1, characterized in that the absorbent member connection means comprises a loop element and the underwear connection means comprises a heat-activated adhesive coating, in particular a hot-melt adhesive coating, so that the combination of the connection member adhered to a piece of underwear is wash-resistant.

11. The sanitary product according to claim 1, characterized in that the material of the base carrier is chosen from paper, polymeric films or nonwovens.

12. The sanitary product according to claim 1, characterized in that the connection member comprises wings on opposing edges, which are provided with a hook element or an adhesive coating.

13. A sanitary product system comprising a sanitary product attachment means according to claim 1 and at least one absorbent member.

14. The sanitary product system according to claim 13, characterized in that the absorbent member is a diaper, a sanitary napkin or pad, panty liner, or an incontinence pad.

15. A method of fixing a sanitary product system according to claim 13 to a piece of underwear, the method comprising the steps of fixing the connection member to the underwear with the underwear connection means and fixing the absorbent member to the connection member with the absorbent member connection means.

16. A method of exchanging a used absorbent member of a sanitary product system according to claim 13 which has been fixed to the piece of underwear, the method comprising the steps of unfixing the used absorbent member from the connection member, in particular while leaving the connection member connected to the piece of underwear, and fixing a new absorbent member to the connection member.

17. A method of exchanging a used absorbent member of a sanitary product system according to claim 13 comprising the sanitary product attachment means in claim 3 which has been fixed to the piece of underwear, the method comprising the steps of peeling the used absorbent member together with the adjacent base carrier from the stack of base carriers, in particular by grabbing the fingerlift area of this base carrier, to reveal a fresh adhesive coating on the connection member and bonding a new absorbent member to the fresh adhesive coating.

18. The method according to claim 17, characterized in that the steps are repeated at least once.

19. The sanitary product of claim 1, wherein a thickness of each layer of the base carrier is in a range of 5 to 100 μm.

* * * * *